United States Patent [19]

Kimsey et al.

[11] Patent Number: 5,176,683

[45] Date of Patent: Jan. 5, 1993

[54] PROSTHESIS PRESS AND METHOD OF USING THE SAME

[76] Inventors: Timothy P. Kimsey, 14801 E. 44th St., Independence, Mo. 64055; William W. Bohn, 6720 Willow La., Mission Hills, Kans. 66208

[21] Appl. No.: 688,683

[22] Filed: Apr. 22, 1991

[51] Int. Cl.$^5$ ............................................. A61F 2/46
[52] U.S. Cl. ..................................... 606/86; 606/99; 606/105; 128/677
[58] Field of Search ...................... 128/677, DIG. 20; 446/197, 198; 606/86, 90, 99, 105; 92/34

[56] References Cited

U.S. PATENT DOCUMENTS

| | | |
|---|---|---|
| 2,823,668 | 2/1958 | Van Court et al. ..... 128/DIG. 20 X |
| 3,279,459 | 10/1966 | Schenker ................ 128/DIG. 20 X |
| 3,319,532 | 5/1967 | Pridham, Jr. ............................ 92/34 |
| 4,102,339 | 7/1978 | Weber et al. ........................ 606/105 |
| 4,372,297 | 2/1983 | Perlin ..................... 128/DIG. 20 X |
| 4,378,009 | 3/1983 | Rowley et al. ......... 128/DIG. 20 X |
| 4,467,801 | 8/1984 | Whiteside . |
| 4,474,177 | 10/1984 | Whiteside . |
| 4,685,447 | 8/1987 | Iversen et al. ........... 128/DIG. 20 X |
| 4,772,287 | 9/1988 | Ray et al. ................ 128/DIG. 20 X |
| 4,898,161 | 2/1990 | Grundei ............................ 606/90 X |
| 4,907,574 | 3/1990 | Hollerbach ............. 128/DIG. 20 X |

FOREIGN PATENT DOCUMENTS

1395352  5/1988  U.S.S.R. .............................. 446/197

OTHER PUBLICATIONS

"Baumanometer ® quality" brochure by W. A. Baum Co., Inc. showing Baum Air-Flo ® Control.
"The P.C.A. Primary Total Knee System" from Howmedica, copyright 1984.
"The Miller/Galante Porous Tivanium Total Knee Because No Two Knees Are Exactly Alike Sizing & Instrumentation Charts" brochure, copyright 1984.
"Dow Corning Wright Whiteside Total Hip System" brochure, copyright 1985 Dow Corning Wright.
"Whiteside Total Hip System Surgical Technique" brochure, copyright 1985 Dow Corning Wright.
"Dow Corning Wright Brief Surgical Procedure for the Whiteside Ortholoc II Total Condylar Knee System" brochure.
"Dow Corning Wright Whiteside Ortholoc II Posterior Stabilized Knee System" brochure, copyright 1987.
"Dow Corning Wright Whiteside Ortholoc II Total Knee System Surgical Technique Total Condylar" brochure, copyright 1987.
"Dow Corning Wright Innovations in Total Knee Design Whiteside Ortholoc II Total Knee Systems" brochure.
"Dow Corning Wright Whiteside Ortholoc II Total Condylar Knee System" brochure.
"Dow Corning Wright Whiteside Ortholoc II-C Total Condylar Knee System": brochure.
"Dow Corning Wright Whiteside Ortholoc II Total Knee System Surgical Techniques Posterior Stabilized" brochure.

(List continued on next page.)

Primary Examiner—Robert A. Hafer
Assistant Examiner—Sam Rimell
Attorney, Agent, or Firm—Hovey, Williams, Timmons & Collins

[57] ABSTRACT

A prosthesis press is provided which broadly includes an expandable force imparting member and an actuating member for expanding the force imparting member between a joint and against at least one prosthetic member. The prosthesis press serves to hold the prosthetic member in place during curing of cement placed between the prosthetic member and the patient's bone, thereby freeing the surgeon to perform other tasks. The force imparting member preferably includes a bellows of resilient plastic material which is expandable upon receipt of fluid pressure therewithin and can at least partially conform to the exposed surfaces of various prosthetic members. The actuating member preferably includes a hand-operated air pump which is connected to the bellows by a conduit, and includes a relief valve for deflating and thus compressing the bellows to enable removal of the same.

3 Claims, 1 Drawing Sheet

OTHER PUBLICATIONS

"Dow Corning Wright Brief Surgical Procedure for the Whiteside Ortholoc II Posterior Stabilized Knee System": copyright 1987.

"Insall/Burstein ® II Modular Knee System" folder containing: Insall/Burstein ® Posterior Stabilized II Modular Knee System Surgical Technique brochure, copyright 1989 Zimmer, Inc.

"Zimmer ® Intramedullary Knee Instrumentation for the Insall/Burstein ® Posterior Stabilized II Knee Surgical Technique" brochure, copyright 1989 Zimmer, Inc.

"Insall/Bursteein ® II Modular Knee System" brochure, copyright 1989 Zimmer, Inc.

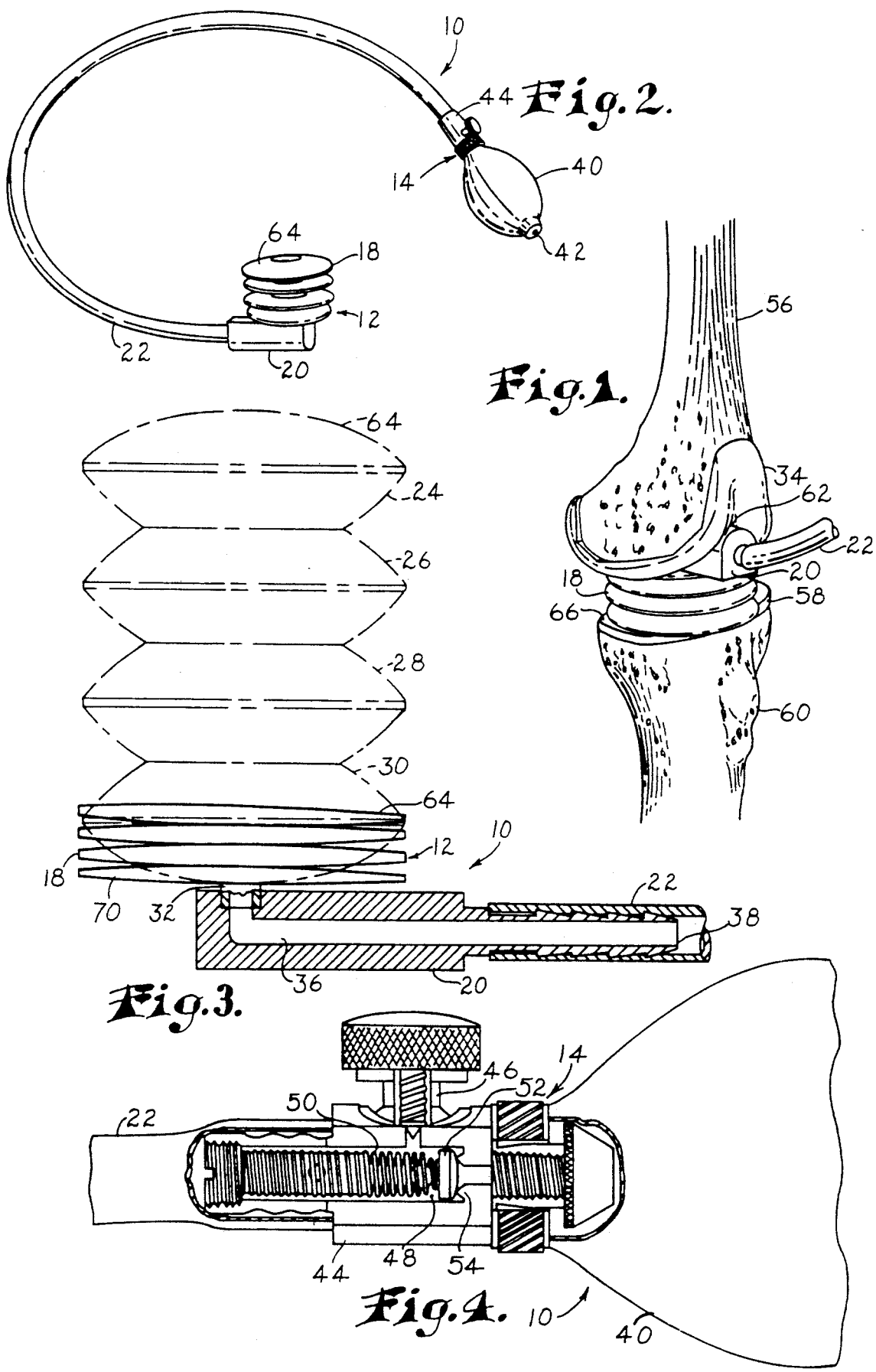

PROSTHESIS PRESS AND METHOD OF USING THE SAME

BACKGROUND OF THE INVENTION

1. Field of the Invention

This invention relates to a press used in retaining a prosthetic member in the bone of a patient during surgery, and more particularly to a device and method for exerting force against the prosthetic member, or a pair of prosthetic members, during curing of cement applied to one of the bone or prosthetic member. The press hereof employs an expandable member which enables the surgeon to conduct other tasks once the press is extended until the cement is sufficiently cured.

2. Description of the Prior Art

The use of prosthetic implants in the bone of a patient are well known in the field of orthopedic surgery. In many instances, the bone or cartilage of the patient has been so damaged by injury or disease as to require that the natural joint be replaced by prosthetic implants. For example, in knee arthroplasty, the joint between the femur and the tibia may require that the proximal tibia and the distal femur are cut transversely and the portions of the removed bone are replaced by prosthetic members and the cartilage replaced with a tibia plastic insert. The components and procedures for this surgical technique are illustrated by a booklet, INSALL/BURSTEIN® Posterior Stabilized II Modular Knee System Surgical Technique and further shown in U.S. Pat. Nos. 4,474,177 and 4,467,801, the contents of which are incorporated herein by reference.

Unfortunately, such surgical procedures are performed with an open incision in the leg or other body member and can be very time consuming. One area which has proven particularly time-consuming is the need to cement the prosthetic members, such as for example, a tibial base or fixation plate and a femoral prosthesis or component, to the bone and allow the cement to sufficiently harden prior to concluding the procedure. The prosthetic members are conventionally of a stainless steel or titanium alloy, and the cement used to secure the prosthetic member to the bone typically requires about twenty minutes to dry or cure. Because the prosthetic member must maintain a good contact with the bone and cement and any voids therebetween reduce the strength of the reconstructed joint, the surgeon typically must manually exert a force of about forty to sixty pounds against the prosthetic member for the entire twenty minutes. In the case of knee replacement surgery, two such twenty minute periods are required—one for the femoral component and one for the tibial base.

As a result, joint replacement operations and knee arthroplasty in particular have been prolonged by the need for the surgeon to personally occupy him or herself with the simple task of holding the prosthetic member in place. During this period, the knee remains open and subject to infection, and the patient is anesthetized. In addition, the surgeon may become fatigued and the contact between the prosthetic member, bone and cement deteriorate if the force applied by the surgeon is substantially lessened. For all these reasons, a need has arisen for a simple, effective tool for limiting the time and effort necessary to ensure a positive contact between the prosthetic member, cement and bone during drying or curing of the cement.

SUMMARY OF THE INVENTION

This need has been largely met by the present invention which frees the surgeon from the mundane task of holding the prosthetic member in place during curing of the cement in surgery. The prosthesis press hereof not only enables the surgeon to perform other critical tasks while the cement cures, but in certain applications virtually halves the total amount of time spent in curing the bone cement with the prosthetic member in place. The prosthesis press includes an expandable member which is held in place by the prosthetic member or members to be cemented, and by expanding against the prosthetic member serves to exert the necessary force to maintain contact between the bone, cement and prosthetic member while the patient's muscles and ligaments provide the required opposing force when the joint is in an extended orientation.

The prosthesis press hereof broadly includes a force imparting member such as an expandable member which is preferably expandable responsive to internal fluid pressure, although other purely mechanical means could be employed. Means for expanding the force imparting member are provided and operably coupled to the force imparting member, including by way of example a fluid pressure generating device. While a variety of such pressure generating devices might be employed, one which is manually actuatable is preferable to provide the necessary control and "feel" for the surgeon. The pressure generating device is fluidically coupled to the expandable member preferably by a conduit, whereby the pressure may be generated from a remote location and applied at the joint by the expandable member.

In preferable forms, the prosthesis press includes a bellows which is made of resilient material and expands in response to air pressure introduced therein. The resilient material allows the bellows to contract when the source of pressure is removed. The pressure generating device is preferably provided with a manually actuatable relief valve to enable the surgeon to bleed off fluid, such as air, when the cement has sufficiently cured. The use of air as a fluid medium is preferable in that leakage poses less of a problem with air than water, and will continue to apply force to the prosthetic members for any extended period notwithstanding small leaks.

The bellows may be provided with a connector to the conduit which is complementarily configured to a recess in one of the prosthetic members. This configuration advantageously serves to locate the bellows in the space to be occupied by the plastic tibial insert. Lateral movement of the bellows during inflation and curing of the cement is avoided as the connector lodges in the recess and is held in position by the expanded bellows and the prosthetic member.

The apparatus hereof advantageously enables the surgeon to apply force to the prosthetic members in a novel procedure. When the surgeon has fully prepared the bone (when only one prosthetic member is to be inserted) or bones, cement is applied to one or both of the prosthetic member and the bone and the prosthetic members are then pressed into position with the joint in flexion. The prosthesis press is then inserted into the area normally occupied by the plastic insert and the joint is extended so that, for example, the femur and tibia are substantially aligned. The force applying member of the press is then expanded so that it exerts force against at least one of the prosthetic members, and preferably both of the prosthetic members simultaneously. The force applying element, which may be a bellows made of resilient material to enable it to substantially conform to the surface of the prosthetic member, is thus expanded and held in place during curing of the cement. When the cement is sufficiently cured, then the bellows is retracted and removed so that the plastic insert may be placed between the prosthetic elements in the conventional manner.

BRIEF DESCRIPTION OF THE DRAWINGS

FIG. 1 is a perspective view of a bellows inserted between a tibial plate and a femoral prosthetic component inserted respectively in the tibia and femur of a patient, with the skin, ligaments and muscles removed for clarity;

FIG. 2 is a perspective view of the prosthesis press hereof;

FIG. 3 is an enlarged, fragmentary side elevational view in partial section of the conduit, connector and bellows components of the prosthesis press hereof; and FIG. 4 is an enlarged, fragmentary side elevational view of the hand pump used to generate fluid pressure for expanding the bellows of the prosthesis press hereof.

DESCRIPTION OF THE PREFERRED EMBODIMENT

Referring now to the drawing, a prosthesis press 10 in accordance with the present invention is shown in FIG. 2 and includes a force imparting member 12 and an actuating member 14 which serves to cause force imparting member to move into a force imparting relationship with a prosthetic member implanted in a patient's bone. The force imparting member 12 is expandable whereby, upon actuation by actuating member 14, the force imparting member increases in size in at least one, and preferably only one, dimension.

In greater detail, force imparting member 12 is preferably a bellows 18 which is expandable responsive to fluid pressure received therein. A connector 20 is positioned in fluid communication with the bellows 18, as best illustrated in FIG. 3, and with a conduit 22. The bellows 18 is preferably made of polyurethane which is tough and resistant to puncture while having good resiliency qualities, although other synthetic resin materials such as polyethylene could be used. The bellows 18 includes four sections 24, 26, 28 and 30 a nipple 32 for receiving air into the interior thereof. It is to be understood that the bellows 18 is preferably dialectric heat sealed of several polyurethane sections so that it presents a relatively small collapsed weight and is substantially fluid-tight and thus retains fluid pressure therein. As shown in FIG. 3, the bellows 18 is expandable from a first contracted position, shown in solid lines in FIG. 3 and preferably of about $\frac{1}{4}$ inch in height, to a second extended position, shown in phantom in FIG. 3, of about 3 inches in height. In actual practice, the bellows would probably need to extend to only about $\frac{3}{4}$ inch in height to properly apply force to the prosthetic members.

Connector 20 is preferably configured to fit complimentarily within a recess of the femoral prosthetic member 34 as shown in FIG. 1. Connector 20 presents a U-shaped cross-section and is preferably constructed of a synthetic resin material such as nylon, Delrin, polyethylene or polypropylene. For use in such applications as knee arthroplasty, the connector is made of a block of nylon about $1\frac{3}{4}$ inches long, $\frac{1}{2}$ inch in width, about $\frac{5}{8}$ inch high and presents an approximately $\frac{1}{4}$ inch radius at the bight of the U. An L-shaped aperture 36 permits the passage of air or other fluid through the connector 20 and is sized to receive nipple 32 at one end thereof as shown in FIG. 3. Conduit 22 is attached to a barbed extension 38 for retaining the conduit 22 in fluid-type connection to the connector 20. Preferably, the extension 38 is integrally molded with the remainder of connector 20.

Turning now to FIG. 4, actuating member 14 is preferably manually actuatable and comprises a pump capable of generating fluidic pressure within bellows 18. Actuating member 14 includes a graspable latex rubber bulb 40 provided with a one-way inlet valve 42 at the distal end thereof and a flow control 44 including a manually actuatable relief valve 46 located at the proximal end thereof and connected to the conduit 22. As shown in FIG. 4, flow control 44 presents an air passageway 48 for the movement of fluid such as air through the actuating member and into the conduit 22. A valve spring 50 biases a valve closure 52 against a valve seat 54 to retain pressurized fluid downstream thereof. Relief valve 46 may be rotated to permit air to escape to the atmosphere and thus depressurize bellows 18. Flow control 44 is commercially available from W.A. Baum Co., Inc. of Copiague, N.Y. under the trademark AIR-FLOW®, and the entire actuating member 14 including bulb 40 may be obtained from the same source as Catalog No. 0661-1890.

In use, the surgeon proceeds through the operation in the conventional manner and as described, for example, in the INSALL/BURSTEIN® Posterior Stabilized II Modular Knee System Surgical Technique, incorporated herein by reference. Prior to finally cementing the femoral prosthetic member 34 to the femur 56 and the tibial plate prosthetic member 58 to the tibia 60 using conventional prosthetic cement, the femur 56 and the tibia 60 are flexed to enable insertion of their respective prosthetic members. Cement is applied to one of the bone and prosthetic members for each respective prosthetic member and then properly inserted by the surgeon. The bellows 18 and connector 20 are inserted so that the connector 20 lies within a cooperatively configured recess 62 of the femoral prosthetic member 34 and the bottom 64 of the bellows 64 is positioned on the exposed face 66 of the tibial plate prosthetic member 58.

The surgeon then extends the femur 56 and tibia 60 into substantial alignment as shown in FIG. 1. It is to be understood that various ligaments and muscles will remain intact and act to hold the femur and tibia against separation. The surgeon then grasps the bulb 40 and, with the relief valve 40 in the closed position, squeezes the bulb several times to transmit air into the bellows 18 causing it to expand in height, roughly as shown in FIGS. 1 and 3. It has been found that the normal grasp by the surgeon is able to generate up to about 20 pounds of force on the bulb, and in the preferred embodiment, the surface area of the bottom surface 64 and top surface 70 of the bellows 18 each occupy about three square inches. Thus, if about 20 pounds per square inch of pressure is generated within the bellows, then approximately 60 pounds of force may be transmitted to each the femoral prosthetic member 34 and the tibial plate prosthetic member 58. The surgeon is then able to perform other tasks while the bellows 18 urges the respective prosthetic members against their respective bones, resisted by the surrounding ligaments and muscles.

To remove the prosthesis press, the surgeon need only rotate the relief valve 46 to allow air to escape from the air passageway 48 and the bellows then are compressed to a contracted position by the force exerted on the femur 56 and the tibia 60 by the surrounding ligaments, such as the tibial collateral, fibular collateral and posterior cruciate, and muscles such as the plantar, sartorius, rectus and gastrocnemius, as well as its own resiliency. The bellows may then be removed and discarded or cleaned for future use.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of their invention as pertains to any apparatus not materially departing from but outside the liberal scope of the invention as set out in the following claims.

We claim:

1. A method of imparting force against a prosthetic member to be attached to a patient's bone to permit cementing of the prosthetic member to the bone, said method comprising the steps of:
    applying cement to one of the prosthetic member and the bone;
    positioning said prosthetic member adjacent to the bone;
    locating an expandable prosthesis press adjacent the prosthetic member; and
    expanding said prosthesis press to bring said press into engagement with said prosthetic member and to impart force against the prosthetic member in the direction of the bone.

2. A method of imparting force against a prosthetic member as set forth in claim 1, including a second prosthetic member to be attached to a second bone, and including the steps of locating said expandable prosthesis press adjacent each of said prosthetic members and imparting force against the same in the direction of the corresponding bones to which each respective prosthetic member is to be attached.

3. A joint replacement prosthesis press for applying a force to a prosthetic component and a prosthetic member during curing of cement used to attach the prosthetic component to one of the patient's bones and the prosthetic member to the patient's opposing bone, and wherein the prosthetic component has a recess, said press comprising:
    an expandable member having a surface and face in opposition to one another, said surface being disposed to engage the prosthetic member in pressure transmitting relationship thereto;
    a transversely elongated, substantially U-shaped bearing member on said face of the expandable member thereof and engageable with said recess of the prosthetic component when the expandable member and bearing member are placed between the prosthetic component and the prosthetic member; and
    means operatively connected to the expandable member for effecting controlled expansion thereof to impart forces of substantial magnitude to said prosthetic component and the prosthetic member respectively during curing of the cement between the prosthetic component and the patient's said one bone and the prosthetic member and the patient's said opposing bone.
    said bearing member located in disposition to be generally complementally received within said recess in the prosthetic component.

* * * * *